(12) United States Patent
Jin et al.

(10) Patent No.: US 11,680,881 B2
(45) Date of Patent: Jun. 20, 2023

(54) PORTABLE SOIL MASS IN-SITU SHEAR TEST DEVICE AND TEST METHOD THEREOF

(71) Applicant: Southwest Jiaotong University, Sichuan (CN)

(72) Inventors: Tao Jin, Sichuan (CN); Xiewen Hu, Sichuan (CN); Liming Zhao, Sichuan (CN); Guanglin Huang, Sichuan (CN); Ruijie Zheng, Sichuan (CN); Xurong He, Sichuan (CN); Song Xue, Sichuan (CN); Mei Han, Sichuan (CN); Chuanjie Xi, Sichuan (CN); Xiangbin Yang, Sichuan (CN)

(73) Assignee: Southwest Jiaotong University, Sichuan (CN)

( * ) Notice: Subject to any disclaimer, the term of this patent is extended or adjusted under 35 U.S.C. 154(b) by 92 days.

(21) Appl. No.: 17/463,547

(22) Filed: Sep. 1, 2021

(65) Prior Publication Data
US 2021/0396637 A1  Dec. 23, 2021

(30) Foreign Application Priority Data
Jan. 15, 2021  (CN) .......................... 202110051470.0

(51) Int. Cl.
*G01N 3/24* (2006.01)
*G01N 33/24* (2006.01)

(52) U.S. Cl.
CPC ............... *G01N 3/24* (2013.01); *G01N 33/24* (2013.01); *G01N 2203/005* (2013.01); *G01N 2203/0025* (2013.01); *G01N 2203/0246* (2013.01); *G01N 2203/0266* (2013.01)

(58) Field of Classification Search
CPC .. G01N 3/24; G01N 33/24; G01N 2203/0025; G01N 2203/005; G01N 2203/0246; G01N 2203/0266; G01N 9/02; G01N 3/02; G01N 19/04; G01N 1/08; G01N 3/12; G01N 19/02; G01N 1/04; G01N 3/22; G01N 3/10; G01N 1/36;
(Continued)

(56) References Cited

U.S. PATENT DOCUMENTS 6,604,432 B1 *  8/2003  Hamblen .................. E02D 1/02
73/594

FOREIGN PATENT DOCUMENTS

CN    108279170 A  *  7/2018
CN    211347748 U  *  8/2020

* cited by examiner

*Primary Examiner* — Brandi N Hopkins (57) ABSTRACT

A portable soil body in-situ shear test device includes: an active force system arranged externally, a passive shear system and an electromagnetic loading system arranged internally, and a ring knife system arranged at a bottom. Compared with the conventional in-situ soil shear strength test device and test method, the present invention is convenient to install and carry as well as simple to operate, and has strong applicability. The present invention is suitable for layered soils with large cross-plate shear test errors, and for soils with different consolidation degrees at various sites and various terrains. A test method adopting the device can simulate the shear strength of the soil mass under different overburden loads without disturbing the mechanical properties of the in-situ soil mass, which has high promotion value in the test of in-situ soil shear strength.

8 Claims, 6 Drawing Sheets

(58) Field of Classification Search
CPC .. G01N 3/08; E02D 33/00; E02D 1/00; E02D 7/22; E02D 1/04; G01D 21/02; G01C 5/00

See application file for complete search history.

PORTABLE SOIL MASS IN-SITU SHEAR TEST DEVICE AND TEST METHOD THEREOF

CROSS REFERENCE OF RELATED APPLICATION

The present invention claims priority under 35 U.S.C. 119(a-d) to CN 202110051470.0, filed Jan. 15, 2021.

BACKGROUND OF THE PRESENT INVENTION

Field of Invention

The present invention relates to a technical field of soil mass in-situ shear test, and more particularly to a portable soil mass in-situ shear test device and a test method thereof.

Description of Related Arts

The shear strength of soil refers to the ultimate strength of soil mass against shear failure, including cohesion (c) and internal friction angle ($\Phi$), which is an important mechanical property of soil, and is also an important parameter to calculate slope stability of road cuts, channels, embankments, and earth dams, as well as to calculate soil pressure for supporting buildings. The in-situ test can determine the engineering mechanical properties of the soil mass at the original position thereof with basically maintained natural structure, natural water content and natural stress state, which can avoid the influence of stress release during the sampling process and obtain more actual test results. Therefore, geotechnical engineers generally believe that in-situ test is the optimal test method to obtain real soil physical and mechanical indexes.

The shear strength index of soil needs to be tested through special instruments. Conventionally, the shear strength of soil is mainly obtained through indoor tests and in-situ tests. Indoor tests include soil direct shear test, triaxial shear test, etc. However, due to the size limitation of the samples in indoor test, the representativeness is poor. In addition, artificiality of the empirical criterion will lead to a large dispersion of the soil shear strength index. More importantly, the indoor soil shear test method generally takes a long time. For example, a set of triaxial shear test of clay soil generally takes about one week. The direct shear test, triaxial shear test, repeated direct shear strength test, and unconfined compressive strength test are the methods for geotechnical testing with relatively solid soils, which all need sampling in the field. Firstly, the shear test sample changes the environmental conditions of the tested soil mass. Secondly, the surface soil is so loose that it is often impossible to get the shear test sample. Therefore, the test is usually unable to perform.

In-situ shear tests of soil mass mainly include large-scale direct shear tests and cross-plate shear tests. However, the conventional large-scale direct shear test has disadvantages such as high costs, long periods, and complicated operations. The cross-plate shear test is a commonly used in-situ shear test, and is one kind of soil mass in-situ tests. It presses a cross-plate head into the soft soil at the bottom of a hole through a borehole, and rotates at a uniform speed. Through a certain measuring system, the torque required for rotation is measured until the soil mass is broken, so as to calculate the shear strength of the soil. The shear strength measured by the cross-plate shear test represents the natural strength of the soil mass in the hole (undrained shear strength). However, the conventional in-situ soil mass shear strength test equipment still has certain limitations:

First, the conventional large-scale in-situ tests often has the disadvantages such as high costs, long periods, and complicated operations, resulting in a small scope of application. They are often used for large-scale important projects since such tests cannot be performed anytime and anywhere.

Second, when the conventional cross-plate shear test is carried out, since there is a time difference between the side and top surfaces of a cylinder to reach shear failure, the strength obtained is not the true peak value, but an average shear strength. Therefore, it cannot truly reflect the true shear strength of the soil mass.

Third, the conventional cross-plate shear test adopts three shear surfaces, namely an upper shear surface, a side shear surface, and a lower shear surface, and the spatial correlation of the three shear surfaces is relatively small. Therefore, there are large errors in the shear strength test of layered soil mass.

Fourth, the conventional in-situ soil mass shear strength test can only measure the shear strength of the soil mass under a natural stress state, and cannot simulate the shear strength and changes of the soil mass when an overburden load exists, and thus causing certain limitations.

SUMMARY OF THE PRESENT INVENTION

In view of the shortcomings of the prior art, an object of the present invention is to provide a portable soil mass in-situ shear test device which is low in cost, convenient to carry, simple to operate, short in test time and accurate in test results.

Accordingly, in order to accomplish the above object, the present invention provides an in-situ soil mass shear strength test device, comprising: a casing having a cylindrical body, wherein an upper part of the casing is sleeved and fixed on an upper bearing outer ring; a shear core, wherein a cylindrical section at an upper part of the shear core is fixed on an upper bearing inner ring, and top surfaces of the shear core, the casing and an upper bearing are aligned; and a circular force turntable, wherein the force turntable is coaxially arranged with the casing, and multiple connecting rods are uniformly and fixedly connected therebetween; wherein a lower part of the casing is fixed on a lower bearing inner ring, and a lower bearing outer ring is fixed on an anchoring counter-pressure plate under a lower bearing; during testing, the anchoring counter-pressure plate is anchored on a surface of a soil mass through anchors; at least two columnar protrusions are arranged at a bottom of the shear core, and a cavity at a lower portion of the shear core contains, from bottom to top, a rubber plug, an electromagnet lower piece and an electromagnet upper piece to apply a pressure on a top surface of a test soil core; a connecting straight rod is movably inserted in central through holes of the rubber plug, the electromagnet upper piece and the electromagnet upper piece; both the connecting straight rod and the electromagnet upper piece are fixed to the shear core; adjacent surfaces of the electromagnet upper piece and the electromagnet lower piece have same poles;

the in-situ soil mass shear strength test device further comprises a ratchet mechanism, wherein a ring-like ratchet groove is provided on an internal wall of the casing; a right-angled triangle ratchet tooth interacts with the ratchet groove, an acute angle vertex of the ratchet tooth is hinged on the shearing core; a ratchet tooth pull rope is fixed between a right-angled vertex of the ratchet tooth and a ratchet tooth reset rod, which is stretched so that the ratchet tooth are pressed against the ratchet groove; a ratchet tooth spring sleeved on the ratchet tooth pull rope; wherein an outer end of the ratchet tooth spring is fixed on the right-angle vertex of the ratchet tooth, and an inner end of the ratchet tooth spring is fixed to a bottom of a cylindrical groove on the shear core; the cylindrical groove is arranged radially along the shear core; the ratchet tooth reset rod extends into an internal hole of the shearing core from top, and the internal hole is located on an extension line of an axis of the cylindrical groove;

multiple force springs are connected between the internal wall of the casing and an external surface of the shear core, and when the casing rotates, the force springs are elongated; a dial which quantitatively indicates a torque is fixed on a top surface of the upper bearing outer ring, and a reading pointer is fixed on a top surface of the upper bearing inner ring;

the in-situ soil mass shear strength test device further comprises a ring knife system to be driven into the soil mass by instrument during the testing, wherein an inner ring knife is arranged inside an outer ring knife with a gap therebetween; two vertical shear plates, which are perpendicular to each other, are fixed in a cavity of the inner ring knife; at least two cylindrical holes for inserting and fixing the columnar protrusions of the shearing core are arranged on a top horizontal edge of the inner ring knife.

Two the ratchet mechanisms are arranged along an axis direction of the shear core with an interval.

A ratchet tooth reset knob is installed on a top portion of the ratchet tooth reset rod protruding from the shear core.

Four the anchoring counter-pressure plates are uniformly distributed and fixed on the lower bearing outer ring.

The internal hole of the shear core is arranged at an eccentric position of the shear core.

A ratchet tooth reset groove is arranged on the shear core.

Cutting edges of the inner ring knife and the outer ring knife are inwardly inclined, and the vertical shearing plates also have cutting edges.

Another object of the present invention is to provide a test method adopting the above device.

Accordingly, in order to accomplish the above object, the present invention provides:

a test method adopting the in-situ soil mass shear strength test device, comprising steps of:

S1: selecting a flat portion of a ground or a slope surface to be tested;

S2: pressing the inner ring knife and the outer ring knife into the soil mass until a desired depth is reached; then further pressing the outer ring knife into the soil mass by a certain depth, in such a manner that the outer ring knife is completely separated from the inner ring knife;

S3: installing the entire in-situ soil mass shear strength test device on the inner ring knife through a ring knife buckle, and connecting a battery to an electromagnet; adjusting an output power of a mobile power supply to set an overburden pressure;

S4: smoothly rotating the force turntable until the soil mass is cut, and reading the dial when a value thereon no longer increases;

S5: then removing and cleaning the in-situ soil mass shear strength test device; and S6: selecting another site with same soil mass texture in a nearby area, changing the output power of the mobile power supply, repeating the steps S1-S5 to obtain different shear strength values under different overburden pressures, and averaging the shear strength values to determine a tested shear strength value of the soil mass.

Compared with the prior art, the present invention has the following beneficial effects:

1. The present invention has a simple structure and is easy to carry and maintain. As an in-situ test equipment, the device has a simple structure and small size, which is easy to carry and requires no sensing device or fixed power supply. The device is more suitable for field tests.

2. The applicability is strong. The present invention is suitable not only for layered soil with large cross-plate shear test error, but also for various sites and various terrains, which can perform soil mass shear strength in-situ test on flat ground as well as on slope surface.

3. Pressure supply is stability. Compared with the normal stress provided by motor servo and man-made mechanical force, the normal stress of the present invention is provided electromagnet. The stable pressure supply ensures the reliability test data.

4. The test period is significantly shortened and the efficiency is improved. Generally, the indoor triaxial shear test requires at least one week, but the method of the present invention is less than one hour for one set of tests, which significantly shortens the test period.

DETAILED DESCRIPTION OF THE PREFERRED EMBODIMENT

Figure 1:
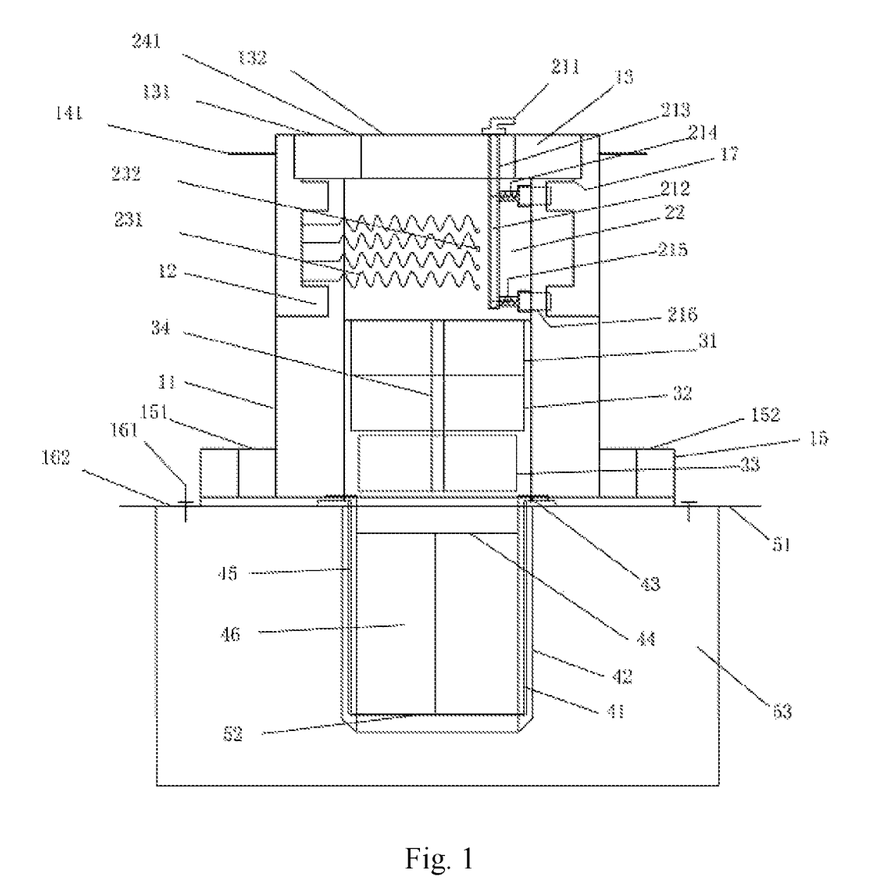
FIG. 1 is a front structural view of a device according the present invention.
Figure 2:
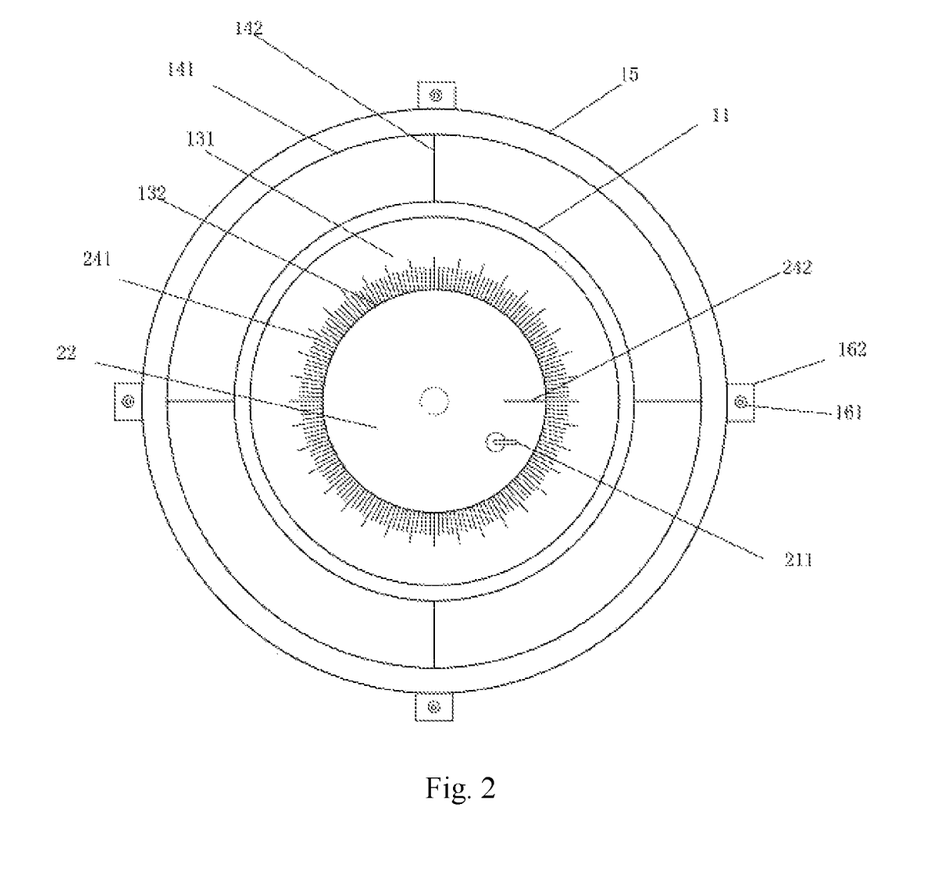
FIG. 2 is a top structural view of the device according the present invention.
Figure 3:
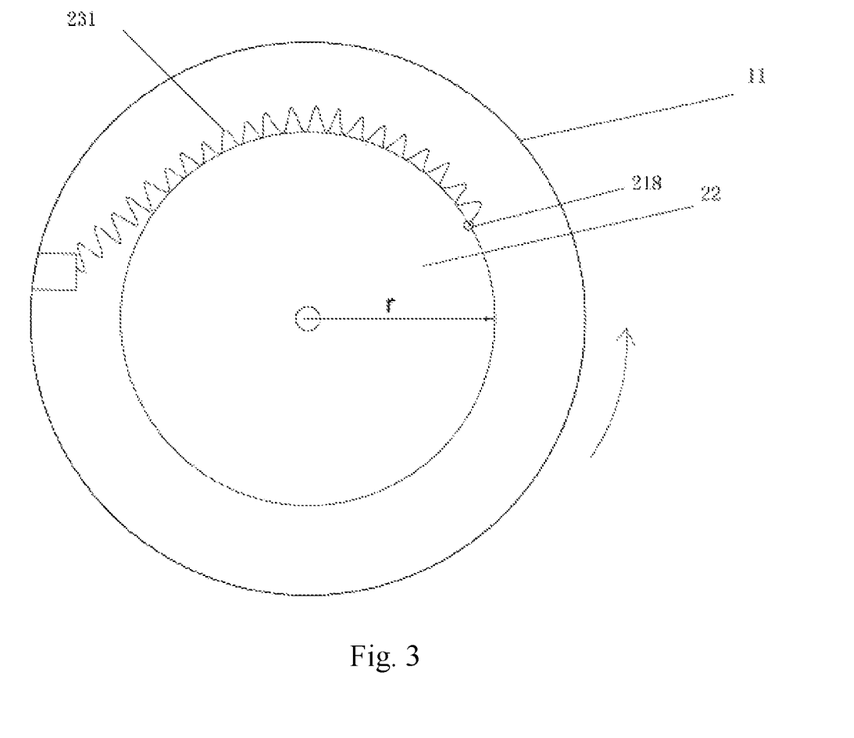
FIG. 3 illustrates a torque measurement principle of the device according the present invention.

Referring to the drawings, embodiments of the present invention will be further described. Element references are: 11—casing, 12—ratchet groove, 13—upper bearing, 131—upper bearing outer ring, 132—upper bearing inner ring, 141—force turntable, 142—connecting rod (of the force turntable), 15—lower bearing, 151—lower bearing inner ring, 152—lower bearing outer ring (having a top horizontal edge), 161—anchor, 162—anchoring counter—pressure plate, 17—upper bearing holder, 211—ratchet tooth reset knob, 212—ratchet tooth reset (knob) rod, 213—internal hole (of the shear core) (referring to FIG. 2, the internal hole is located at an eccentric position of the shear core), 214—ratchet tooth spring, 215—ratchet tooth pull rope, 216—ratchet tooth, 217—ratchet tooth reset groove, 218—ratchet tooth hinge joint, 219—cylinder groove, 22—shear core (comprising an upper cylinder with a smaller diameter, a middle cylinder with a larger diameter, a lower cylinder whose inner diameter is the same as the diameter of the middle cylinder, and an opened bottom), 231—force spring (multiple force springs are arranged along different circumferences of the shear core), 232—force spring fixing nut, 241—dial, 242—reading pointer, 31—electromagnet upper piece, 32—electromagnet lower piece, 33—rubber plug, 34—connecting straight rod, 41—inner ring knife, 42—outer ring knife, 43—ring knife buckle, 44—vertical shear plate (of the inner ring knife) (having cutting edge), 45—ring knife gap, 46—test soil core (cylinder), 51—ground surface, 52—shear surface to be tested, 53—soil mass to be tested;

Referring to FIG. 1, An in-situ soil mass shear strength test device, comprising: a casing 11 having a cylindrical body, wherein an upper part of the casing 11 is sleeved and fixed on an upper bearing outer ring 131; a shear core 22, wherein a cylindrical section at an upper part of the shear core 22 is fixed on an upper bearing inner ring 132, and top surfaces of the shear core 22, the casing 11 and an upper bearing 13 are aligned; and a circular force turntable 141, wherein the force turntable 141 is coaxially arranged with the casing 11, and multiple connecting rods 142 are uniformly and fixedly connected therebetween; wherein a lower part of the casing 11 is fixed on a lower bearing inner ring 151, and a lower bearing outer ring 152 is fixed on an anchoring counter-pressure plate 162 under a lower bearing 15; during testing, the anchoring counter-pressure plate 162 is anchored on a surface 51 of a soil mass 53 through anchors 161; at least two columnar protrusions are arranged at a bottom of the shear core 22, and a cavity at a lower portion of the shear core 22 contains, from bottom to top, a rubber plug 33, an electromagnet lower piece 32 and an electromagnet upper piece 31 to apply a pressure on a top surface of a test soil core 46; a connecting straight rod 34 is movably inserted in central through holes of the rubber plug 33, the electromagnet upper plate 32 and the electromagnet upper piece 31; both the connecting straight rod 34 and the electromagnet upper piece 31 are fixed to the shear core 22; adjacent surfaces of the electromagnet upper plate 31 and the electromagnet lower piece 32 have same poles;

the in-situ soil mass shear strength test device further comprises a ratchet mechanism, wherein a ring-like ratchet groove 12 is provided on an internal wall of the casing 11; a right-angled triangle ratchet tooth 216 interacts with the ratchet groove 12, and an acute angle vertex of the ratchet tooth 216 is hinged on the shearing core 22; a ratchet tooth pull rope 215 is fixed between a right-angled vertex of the ratchet tooth 216 and a ratchet tooth reset rod 212, which is stretched so that the ratchet tooth are pressed against the ratchet groove; a ratchet tooth spring 214 is sleeved on the ratchet tooth pull rope 215; an outer end of the ratchet tooth spring 214 is fixed on the right-angle vertex of the ratchet tooth 216, and an inner end of the ratchet tooth spring 214 is fixed to a bottom of a cylindrical groove 219 on the shear core 22; the cylindrical groove 219 is arranged radially along the shear core 22; the ratchet tooth reset rod 212 extends into an internal hole 213 of the shearing core from top, and the internal hole 213 is located on an extension line of an axis of the cylindrical groove 219;

multiple force springs 231 are connected between the internal wall of the casing 11 and an external surface of the shear core 22, and when the casing 11 rotates, the force springs 231 are elongated; a dial 241 which quantitatively indicates a torque is fixed on a top surface of the upper bearing outer ring 131, and a reading pointer 242 is fixed on a top surface of the upper bearing inner ring 132;

the in-situ soil mass shear strength test device further comprises a ring knife system to be driven into the soil mass 53 by instrument during the testing, wherein an inner ring knife 41 is arranged inside an outer ring knife 42 with a gap therebetween; two vertical shear plates 44, which are perpendicular to each other, are fixed in a cavity of the inner ring knife 41; at least two cylindrical holes for inserting and fixing the columnar protrusions of the shearing core 22 are arranged on a top horizontal edge of the inner ring knife 41 (see FIGS. 2 and 3). The rubber plug, the electromagnet lower piece 32 and the electromagnet upper piece 31 are all disc-shaped. The casing 11 and the shear core 22 are coaxial. Referring to FIG. 1, two ratchet mechanisms are arranged along an axis direction of the shear core 22 with an interval.

Referring to FIGS. 1 and 2, a portable soil mass in-situ shear test device comprises an active force system, a passive shear system, an electromagnetic loading system, and a ring knife system.

The active force system is located at an outermost part of the entire device, and comprises a casing 11, an upper bearing 13 for fixing a shear core 22, a lower bearing 15 for connecting the casing 11 and an anchoring counter-pressure plate 162, a force turntable 141, and the anchoring counter-pressure plate.

The cylindrical casing 11 is formed by an encircling external wall of the casing 11. An upper part of an internal wall of the casing 11 is rigidly connected to two rings of ratchet grooves 12 evenly distributed from top to bottom. An upper bearing holder 17 is provided above the ratchet grooves 12 for fixing the upper bearing 13. An upper part of the external wall of the casing 11 is rigidly connected to the force turntable 141. The force turntable 141 and the external wall of the casing 11 are welded and connected by a connecting rod 142, so as to transmitting a torque to the passive shear system through the force turntable 141 during the test. The upper bearing 13 is located at an upper part of the device, whose top surface is aligned with a top surface of the cylindrical casing 11. An external side wall of an upper bearing outer ring 131 is rigidly connected to the internal wall of the casing 11, and an upper bearing inner ring 132 is rigidly connected to the shear core 22 at a device core. A lower bearing inner ring 151 is rigidly connected to the external wall of the casing 11 to ensure that the entire active force system can rotate normally relative to the ground 51. A lower part of the lower bearing outer ring 152 is welded to the anchoring counter-pressure plates 162. An anchoring device is divided into the anchoring counter-pressure plates 162 and anchors 161. Four anchoring counter-pressure plates 162 are evenly distributed and fixed on the lower bearing outer ring 152. The anchoring counter-pressure plates 162 is aligned with the ground surface. Each anchoring counter-pressure plates 162 has a small hole in a middle, and the anchors fixes the entire device in the soil mass 53 through the small hole, so as to prevent the entire device from relative movement in a vertical direction except for rotation.

The passive shearing system is located at the device core, comprising: a ratchet tooth reset knob 211, a ratchet tooth reset rod 212, a ratchet tooth spring 214, a ratchet tooth pull rope 215, a ratchet tooth 216, the shearing core 22, a force spring 231, force spring fixing nut 232, a dial 241, and a reading pointer 242.

Figure 4:
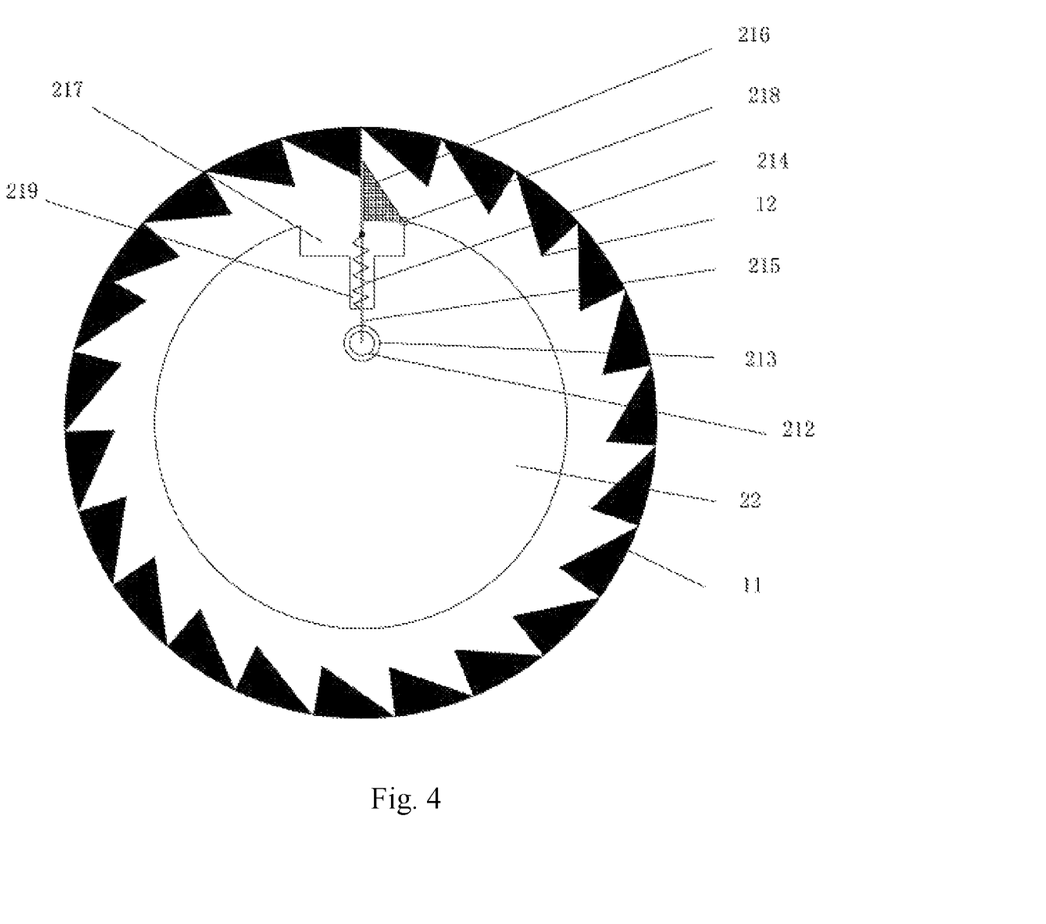
FIG. 4 illustrates a ratchet working principle of the device according the present invention.

Referring to FIG. 1, an internal hole 213 is arranged near a middle of the shear core 22 to contain a ratchet tooth reset rod 212 which extends out from the shear core 22, and the ratchet tooth reset rod 212 extends out from a top end of the shear core 22 to connect a ratchet tooth reset knob 211. The ratchet tooth reset knob 211 is located on a top surface of the entire device. a middle part and a lower part of the ratchet tooth reset rod 212 are respectively connected to high-strength nylon wires, namely ratchet tooth pull ropes 215. One end of the ratchet tooth pull rope 215 is connected to the ratchet tooth reset rod 212, and the other end is connected to the ratchet tooth 216. Referring to FIG. 4, in addition to the ratchet tooth pull rope 215, a ratchet tooth spring 214 is connected between the ratchet tooth 216 and the clamping ratchet tooth reset rod 212. One end of the ratchet tooth spring is connected to a lower end of the ratchet tooth 216, and the other end is fixed in a cylindrical groove 219 of the shear core 22. The other end of the lower part of the ratchet tooth 216 is hinged to edges of the shear core 22 and a ratchet tooth reset groove 217, namely connected by a ratchet tooth hinge joint 218. A working principle is: after rotating the ratchet tooth reset knob 211, an effective length of the ratchet tooth pull rope 215 becomes shorter (wound on the ratchet tooth reset rod 212), and the ratchet tooth spring 214 shrinks, causing the ratchet tooth 216 to rotate around the ratchet tooth hinge joint 218 and enter the ratchet tooth reset groove 217; when the ratchet tooth reset knob 211 is released, the effective length of the ratchet tooth pull cord 215 becomes longer, and the ratchet tooth spring 214 releases an elastic potential energy and extends, thereby resetting the ratchet tooth 216. The ratchet tooth reset groove 217 is a cuboid set on the shear core 22, whose size is equivalent to that of the ratchet tooth 216, and the ratchet tooth reset groove 217 is arranged horizontally. The cylindrical groove 219 is arranged along an inner diameter direction of the shear core 22 for accommodating the ratchet tooth spring 214, which provides a working space for the ratchet tooth 216 and the ratchet tooth spring 214, ensuring normal expansion and rotation. The force spring fixing nut 232 is fixed on the external wall of the shear core 22, to which the force spring 231 is connected. The other end of the force spring 231 is rigidly connected to the casing 11 for transmitting external torque to the shear core 22 (see FIGS. 1 and 3).

Referring to FIG. 2, the dial 241 and the reading pointer 242 are arranged on the top surface of the device to quantify the torque. The dial 241 is located inside the upper bearing outer ring 131, and will rotate with the casing 11 during working. The reading pointer 242 is located on the upper bearing inner ring 132, and is aligned with the dial 241. The reading pointer 242 remains stationary relative to the shear core 22.

The electromagnetic loading system is located at a lower part of the shear core 22, wherein the electromagnet upper piece 31, the electromagnet lower piece 32 and a rubber plug 33 are sequentially installed from top to bottom, and are connected in series through a connecting straight rod 34 in centers thereof.

Referring to FIG. 1, there is a pair of electromagnets at the lower part of the shear core 22. The electromagnets are powered by a mobile battery. An external load can be controlled by adjusting an output power of the mobile power. The rubber plug 33 is provided under the electromagnet lower piece 32. The same magnetic poles of the electromagnets are opposed to each other to generate mutual repulsion when energized. A bottom surface of the rubber plug 33 is in directly contact with the top surface of a test soil core 46, and a top surface of the rubber plug 33 is in contact with a bottom surface of the electromagnet lower piece 32, thereby transmitting a pressure to the surface of the test soil core 46. The electromagnet upper piece 31, the electromagnet lower piece 32, and the rubber plug 33 are connected by a connecting straight rod 34 in the centers thereof to ensure vertically moving only and avoid horizontally moving.

Figure 5:
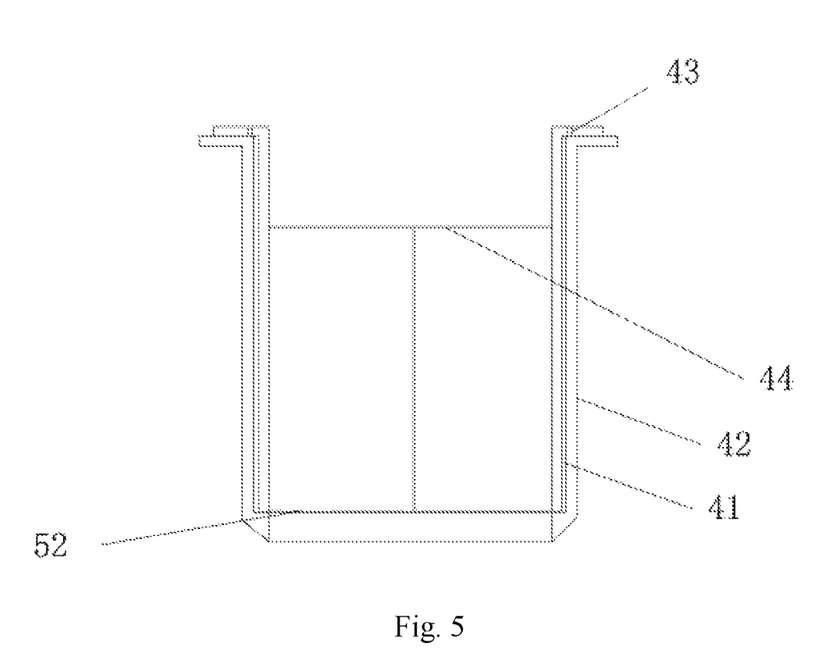
FIG. 5 is a front view of a ring knife system of the device according the present invention.
Figure 6:
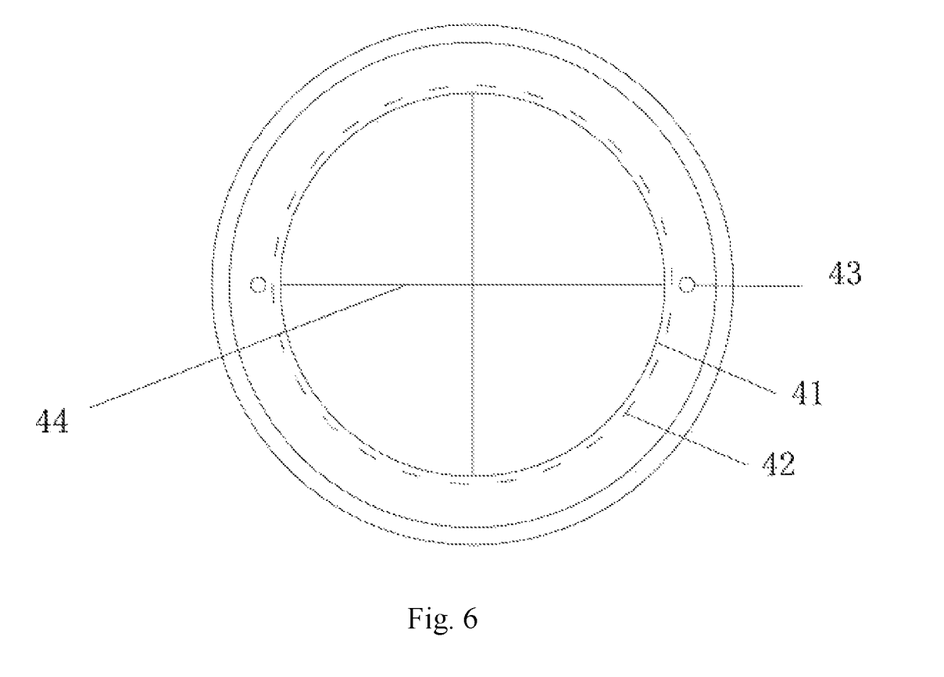
FIG. 6 is a top view of the ring knife system of the device according the present invention.

The ring knife system is located at a lowest part of the entire device, which is inserted into the soil mass 53 during working, the outer ring knife 42 is located at an outermost side, a size of the inner ring knife 41 is slightly smaller than that of the outer ring knife 42. Vertical shear plates 44 are welded to an internal wall of the inner ring knife 41.

Figure 7:
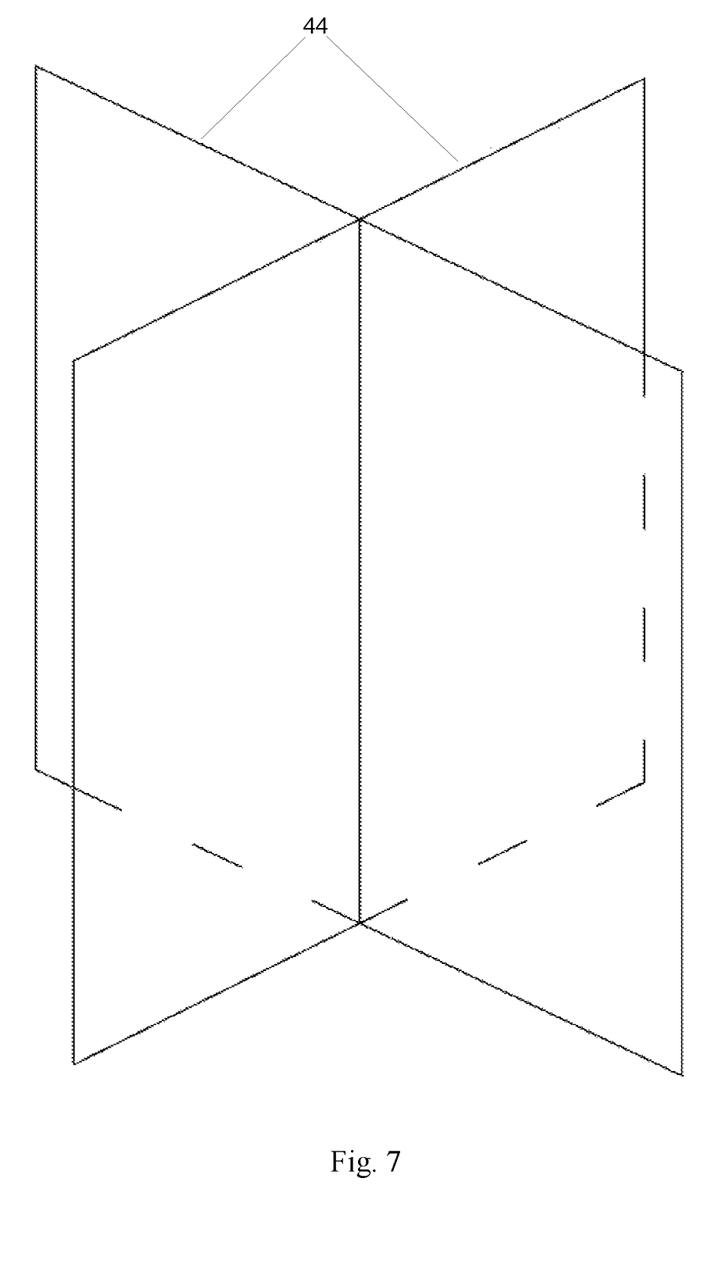
FIG. 7 is a sketch view of vertical shear plates of an inner ring knife of the device according the present invention.

Referring to FIGS. 5 and 6, at least two cylindrical holes are arranged on an upper part of the inner ring knife 41, which are opposite to the two short cylindrical protrusions (inserted into the holes) at the lower part of the shear core 22. The shear core 22 and the inner ring knife 41 are connected by ring knife buckles 43 (4-6 pieces can be used, uniformly distributed), thereby transmitting the torque from the passive shear system to the ring knife system from top to bottom. Two vertical rectangular vertical shear plates 44 are weld inside the inner ring cutter 41 (see FIG. 7) to avoid relative rotation between the test soil core 46 and the inner ring cutter 41 during working and ensure that all the torque is transmitted to the shear surface 52 of the test soil core 46. The size of the outer ring knife 42 is slightly larger than that of the inner ring knife 41. In addition, cutting edges of the inner ring knife 41 and the outer ring knife 42 are inwardly inclined, and there is a ring knife gap 45 between the inner ring knife 41 and the outer ring knife 42, so as to prevent a friction, caused by direct contact between the inner ring knife 41 and the outer ring knife 42, from affecting the test result.

A principle of an in-situ soil mass shear test method of the present invention is: in the in-situ soil mass shear test device, the inner and outer ring knives have a cylindrical thin-walled rigid structure with no bottom, and a blade-like structure is provide at a bottom portion. The inner and outer ring knives can be easily inserted into the soil mass, and inwardly inclined cutting edges are provided at bottoms (see FIG. 5, the lower part of the outer ring cutter 41 has the inwardly inclined cutting edges), so that a shear ring can be inserted downwards into the soil mass with minimal resistance.

Referring to FIGS. 3 and 4, a mechanics principle of the test method of the present invention is to use an instrument to drive the inner and outer ring knives into the soil mass 53 for measuring in situ soil mass shear strength at a test point. After the ring knives reach a desired depth, the outer ring knife 42 is further pressed into the soil mass 53 by a certain depth, in such a manner that the outer ring knife 42 is completely separated from the inner ring knife 41. By applying an external force, the force turntable 141 can be rotated, in such a manner that the inner ring knife 41 of the shear device is driven to cut the soil mass 53. At the same time, the force spring 231 is elongated. Before the soil mass 53 is damaged by shearing, the shear core 22 remains stationary relative to the test soil core 46, and there is a relative counterclockwise rotation between the casing 11 and the shear core 22. Referring to FIG. 4, when the outer casing 11 rotates counterclockwise relative to the inner shear core 22, due to a unidirectional property of the ratchet tooth 216, relative movement between the casing 11 and the shear core 22 will not be hindered by the ratchet tooth 216. At this time, a magnitude of the external force applied is equal to a force on the force spring 231, which is balanced by a shear resistance of the test soil core 46. As the external force increases smoothly, the shear stress on the shear surface 52 increases with the increase of the torque. When a maximum torque $M_{max}$ is reached, the soil mass 53 will be broken along a bottom surface of the test soil core 46, and the shear stress on the bottom surface of the cylindrical test soil core 46 is equal to a shear strength $\tau_f$ of the soil. Meanwhile, an elastic force of the face spring 231 is greater than the shear resistance of the shear surface 52 of the test soil core 46 after shear failure, so the shear core 22 has a tendency to relatively rotate counterclockwise relative to the casing 11.

At this time, the ratchet tooth 216 is engaged with the ratchet groove 12 for functioning, in such a manner that relative rotation between the casing 11 and the shear core 22 no longer occurs. As a result, a value indicated by the reading pointer 242 no longer changes.

The elastic force of the force spring 231 can be calculated by Hooke's law:

$$F = k \cdot \Delta x$$

wherein k is a stiffness coefficient of the force spring 231; $\Delta x$ is a total extension of the force spring 231.

A conversion relationship between the maximum torque $M_{max}$ and the elastic force is:

$$M_{max} = F \cdot r$$

wherein: F is a total elastic force of the force spring 231; r is a radius of the shear core 22 where the force spring 231 is surround.

When the inner and outer ring knives are inserted into the soil mass, the sheared soil mass 53 is a cylindrical soil core, wherein a top surface thereof is the ground surface 51, and the top surface and side surface of the test soil core 46 are through surfaces, which means torsional moment of the top surface and side surface is 0. Therefore, $M_{max}$ is the torsional moment produced by the shear strength of the shear surface 52 of the test soil core 46 on the center of the circle, which is:

$$M_{max} = \int_0^{\frac{D}{2}} \tau_f \cdot 2\pi r \cdot r dr = \frac{\pi D^3 \tau_f}{12}$$

$$\tau_f = \frac{12 M_{max}}{\pi D^3}$$

wherein: $\tau_f$ is the shear strength of the shear surface 52 of the test soil core 46;

D is a diameter of the shear surface 52 of the test soil core 46.

According to the above calculation, the shear strength $\tau_f$ of the soil mass can be obtained.

A test method adopting the above in-situ soil mass shear strength test device will be described below, comprising steps of:

S1: selecting a flat portion of a ground or a slope surface to be tested;

S2: pressing the inner ring knife 41 and the outer ring knife 42 into the soil mass 53 until a desired depth is reached; then further pressing the outer ring knife 42 into the soil mass 53 by a certain depth, in such a manner that the outer ring knife 42 is completely separated from the inner ring knife 41;

S3: installing the entire in-situ soil mass shear strength test device on the inner ring knife 41 through a ring knife buckle 43, and connecting a battery to an electromagnetic loading system; adjusting an output power of a mobile power supply to set an overburden pressure;

S4: smoothly rotating the force turntable 141 until the soil mass 53 is cut, and reading the dial 241 when a value thereon no longer increases;

S5: then removing and cleaning the in-situ soil mass shear strength test device; and S6: selecting another site with same soil mass texture in a nearby area, changing the output power of the mobile power supply, repeating the steps S1-S5 to obtain different shear strength values, and averaging the shear strength values to determine a tested shear strength value of the soil mass 53.

What is claimed is:

1. An in-situ soil mass shear strength test device, comprising: a casing (11) having a cylindrical body, wherein an upper part of the casing (11) is sleeved and fixed on an upper bearing outer ring (131); a shear core (22), wherein a cylindrical section at an upper part of the shear core (22) is fixed on an upper bearing inner ring (132), and top surfaces of the shear core (22), the casing (11) and an upper bearing (13) are aligned; and a circular force turntable (141), wherein the force turntable (141) is coaxially arranged with the casing (11), and multiple connecting rods (142) are uniformly and fixedly connected therebetween; wherein a lower part of the casing (11) is fixed on a lower bearing inner ring (151), and a lower bearing outer ring (152) is fixed on an anchoring counter-pressure plate (162) under a lower bearing (15); during testing, the anchoring counter-pressure plate (162) is anchored on a surface (51) of a soil mass (53) through anchors (161); at least two columnar protrusions are arranged at a bottom of the shear core (22), and a cavity at a lower portion of the shear core (22) contains, from bottom to top, a rubber plug (33), an electromagnet lower piece (32) and an electromagnet upper piece (31) to apply a pressure on a top surface of a test soil core (46); a connecting straight rod (34) is movably inserted in central through holes of the rubber plug (33), the electromagnet lower piece (32) and the electromagnet upper piece (31); both the connecting straight rod (34) and the electromagnet upper piece (31) are fixed to the shear core (22); adjacent surfaces of the electromagnet upper piece (31) and the electromagnet lower piece (32) have same poles;

the in-situ soil mass shear strength test device further comprises a ratchet mechanism, wherein a ring-like ratchet groove (12) is provided on an internal wall of the casing (11); a right-angled triangle ratchet tooth (216) interacts with the ratchet groove (12), and an acute angle vertex of the ratchet tooth (216) is hinged on the shearing core (22); a ratchet tooth pull rope (215) is fixed between a right-angled vertex of the ratchet tooth (216) and a ratchet tooth reset rod (212); a ratchet tooth spring (214) is sleeved on the ratchet tooth pull rope (215); an outer end of the ratchet tooth spring (214) is fixed on the right-angle vertex of the ratchet tooth (216), and an inner end of the ratchet tooth spring (214) is fixed to a bottom of a cylindrical groove (219) on the shear core (22); the cylindrical groove (219) is arranged radially along the shear core (22); the ratchet tooth reset rod (212) extends into an internal hole (213) of the shearing core from top, and the internal hole (213) is located on an extension line of an axis of the cylindrical groove (219);

multiple force springs (231) are connected between the internal wall of the casing (11) and an external surface of the shear core (22), and when the casing (11) rotates, the force springs (231) are elongated; a dial (241) which quantitatively indicates a torque is fixed on a top surface of the upper bearing outer ring (131), and a reading pointer (242) is fixed on a top surface of the upper bearing inner ring (132);

the in-situ soil mass shear strength test device further comprises a ring knife system to be driven into the soil mass (53) by a force turntable (141) during the testing, wherein an inner ring knife (41) is arranged inside an outer ring knife (42) with a gap therebetween; two vertical shear plates (44), which are perpendicular to each other, are fixed in a cavity of the inner ring knife (41); at least two cylindrical holes for inserting and fixing the columnar protrusions of the shearing core (22) are arranged on a top horizontal edge of the inner ring knife (41).

2. The in-situ soil mass shear strength test device, as recited in claim 1, wherein two the ratchet mechanisms are arranged along an axis direction of the shear core (22) with an interval.

3. The in-situ soil mass shear strength test device, as recited in claim 1, wherein a ratchet tooth reset knob (211) is installed on a top portion of the ratchet tooth reset rod (212) protruding from the shear core (22).

4. The in-situ soil mass shear strength test device, as recited in claim 1, wherein four anchoring counter-pressure plates (162) are uniformly distributed and fixed on the lower bearing outer ring (152).

5. The in-situ soil mass shear strength test device, as recited in claim 1, wherein the internal hole (213) of the shear core (22) is arranged at an eccentric position of the shear core (22).

6. The in-situ soil mass shear strength test device, as recited in claim 1, wherein a ratchet tooth reset groove (217) is arranged on the shear core (22).

7. The in-situ soil mass shear strength test device, as recited in claim 1, wherein cutting edges of the inner ring knife (41) and the outer ring knife (42) are inwardly inclined, and the vertical shearing plates (44) also have cutting edges.

8. A test method adopting the in-situ soil mass shear strength test device as recited in claim 1, comprising steps of:
- S1: selecting a flat portion of a ground or a slope surface to be tested;
- S2: pressing the inner ring knife (41) and the outer ring knife (42) into the soil mass (53) until a desired depth is reached; then further pressing the outer ring knife (42) into the soil mass (53) by a certain depth, in such a manner that the outer ring knife (42) is completely separated from the inner ring knife (41);
- S3: installing the entire in-situ soil mass shear strength test device on the inner ring knife (41) through a ring knife buckle (43), and connecting a battery to an electromagnetic loading system; adjusting an output power of a mobile power supply to set an overburden pressure;
- S4: smoothly rotating the force turntable (141) until the soil mass (53) is cut, and reading the dial (241) when a value thereon no longer increases;
- S5: then removing and cleaning the in-situ soil mass shear strength test device; and
- S6: selecting another site with same soil mass texture in a nearby area, repeating the steps S1-S5 to obtain different shear strength values, and averaging the shear strength values to determine a tested shear strength value of the soil mass (53).

\* \* \* \* \*